United States Patent
Wu et al.

(10) Patent No.: US 8,835,581 B2
(45) Date of Patent: Sep. 16, 2014

(54) NEUTRAL LAYER POLYMER COMPOSITION FOR DIRECTED SELF ASSEMBLY AND PROCESSES THEREOF

(75) Inventors: Hengpeng Wu, Hillsborough, NJ (US); Orest Polishchuk, Bayonne, NJ (US); Yi Cao, Clinton, NJ (US); SungEun Hong, Basking Ridge, NJ (US); Jian Yin, Bridgewater, NJ (US); Guanyang Lin, Whitehouse Station, NJ (US); Margareta Paunescu, Clinton, NJ (US); Mark Neisser, Whitehosue Station, NJ (US)

(73) Assignee: AZ Electronic Materials (Luxembourg) S.A.R.L., Luxembourg (LU)

(*) Notice: Subject to any disclaimer, the term of this patent is extended or adjusted under 35 U.S.C. 154(b) by 155 days.

(21) Appl. No.: 13/492,125

(22) Filed: Jun. 8, 2012

(65) Prior Publication Data

US 2013/0330668 A1    Dec. 12, 2013

(51) Int. Cl.
*C08F 4/04* (2006.01)
*C07C 245/04* (2006.01)

(52) U.S. Cl.
CPC .............. *C08F 4/04* (2013.01); *C07C 245/04* (2013.01)
USPC ........ 526/219; 526/219.1; 526/319; 526/347; 534/573; 534/588

(58) Field of Classification Search
None
See application file for complete search history.

(56) References Cited

U.S. PATENT DOCUMENTS

| | | | |
|---|---|---|---|
| 3,161,630 A * | 12/1964 | Quiby et al. | 534/886 |
| 3,285,949 A * | 11/1966 | Siebert | 558/358 |
| 3,474,054 A | 10/1969 | White | |
| 4,200,729 A | 4/1980 | Calbo | |
| 4,251,665 A | 2/1981 | Calbo | |
| 4,698,394 A | 10/1987 | Wong | |
| 5,136,029 A * | 8/1992 | Furukawa et al. | 534/726 |
| 5,187,019 A | 2/1993 | Calbo et al. | |
| 5,446,125 A | 8/1995 | Honda et al. | |
| 5,674,662 A | 10/1997 | Szmanda et al. | |
| 5,929,204 A | 7/1999 | Noguchi et al. | |
| 6,512,020 B1 | 1/2003 | Asakura et al. | |
| 7,471,614 B2 | 12/2008 | Frommer et al. | |
| 7,521,094 B1 | 4/2009 | Cheng et al. | |
| 7,560,141 B1 | 7/2009 | Kim et al. | |
| 7,846,502 B2 | 12/2010 | Kim et al. | |
| 8,017,194 B2 | 9/2011 | Colburn et al. | |
| 8,226,838 B2 | 7/2012 | Cheng et al. | |
| 8,309,278 B2 | 11/2012 | Yang et al. | |
| 8,491,965 B2 | 7/2013 | Cheng et al. | |
| 8,686,109 B2 | 4/2014 | Yin et al. | |
| 8,691,925 B2 | 4/2014 | Wu et al. | |
| 2004/0157948 A1 * | 8/2004 | Schlueter | 522/32 |
| 2007/0276104 A1 * | 11/2007 | Harruna et al. | 526/147 |
| 2008/0299353 A1 | 12/2008 | Stoykovich et al. | |
| 2008/0318005 A1 | 12/2008 | Millward | |
| 2009/0035668 A1 | 2/2009 | Breyta et al. | |
| 2009/0087653 A1 | 4/2009 | Nealey et al. | |
| 2009/0179002 A1 | 7/2009 | Cheng et al. | |
| 2009/0196488 A1 | 8/2009 | Nealey et al. | |
| 2010/0124629 A1 | 5/2010 | Gopalan et al. | |
| 2011/0147984 A1 | 6/2011 | Cheng et al. | |
| 2012/0285929 A1 | 11/2012 | Matsumura et al. | |
| 2013/0012618 A1 | 1/2013 | Hiro et al. | |
| 2013/0078576 A1 | 3/2013 | Wu et al. | |
| 2013/0330668 A1 | 12/2013 | Wu et al. | |

FOREIGN PATENT DOCUMENTS

| | | |
|---|---|---|
| CA | 1 293 090 C | 12/1991 |
| EP | 0 227 124 A2 | 7/1987 |
| EP | 1 095 711 A2 | 5/2001 |
| JP | 58-225103 A | 12/1983 |
| JP | 2003-48929 A | 2/2003 |
| JP | 2003-238682 A | 8/2003 |
| JP | 2008-88368 A | 4/2008 |
| JP | 2010-260883 A | 11/2010 |
| JP | 2011-18778 A | 1/2011 |
| WO | WO 2012/022390 A1 | 2/2012 |
| WO | WO 2012/161106 A1 | 11/2012 |

OTHER PUBLICATIONS

Serhatli, Polymer Bulletin 34, 539-546 (1995).*
Sugiyama, Macromol. Chem. Phys. 195, 1341-1352 (1994).*
Koji Asakawa et al., "Nanopatterning with Microdomains of Block Copolymers using Reactive-Ion Etching Selectivity", Jpn. J. Appl. Phys. 41 No. 10, pp. 6112-pp. 6118 (2002).
C. T. Black et al., "Integration of self-assembled diblock copolymers for semiconductor capacitor fabrication," Applied Physics Letters vol. 79 No. 3, pp. 409-pp. 411 (2001).
T. Thurn-Albrecht et al., "Ultrahigh-Density Nanowire Arrays Grown in Self-Assembled. Diblock Copolymer Templates", Science Vo. 290, pp. 2126-pp. 2129 (2000).
Ghislain David et al., "Synthesis of α,ω-Phosponate Polysterene via Dead End Polymerization, Phosporus, Sulfur, and Silicon", Taylor & Francis Inc, US, vol. 179 No. 12, pp. 2627-pp. 2634 (2004).

(Continued)

*Primary Examiner* — Robert C Boyle
(74) *Attorney, Agent, or Firm* — Sangya Jain

(57) ABSTRACT

The present invention relates to a novel polymeric composition comprising a novel polymer having two or more repeat units and a terminus having the structure (1):

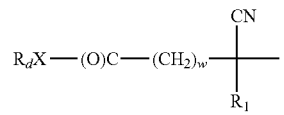

wherein $R_1$ represents a $C_1$-$C_{20}$ substituted or unsubstituted alkyl group, w is a number from 1-8, X is oxygen (O) or nitrogen (N), and $R_d$ is a reactive group. The invention also relates to a process for forming a pattern using the novel polymeric composition. The invention further relates to a process of making the novel polymer.

15 Claims, No Drawings

(56) References Cited

OTHER PUBLICATIONS

Form PCT/ISA/220, Form PCT/ISA/210, and Form PCT/ISA/237 dated Feb. 26, 2013 for PCT/IB2012/001905, which corresponds to U.S. Appl. No. 13/164,869.

Form PCT/ISA/220, Form PCT/ISA/210, and Form PCT/ISA/237 dated Jul. 11, 2013 for PCT/EP2013/053548, which corresponds to U.S. Appl. No. 13/416,669.

Form PCT/ISA/220, Form PCT/ISA/210, and Form PCT/ISA/237 dated Aug. 28, 2013 for PCT/EP2013/001423, which corresponds to U.S. Appl. No. 13/492,125.

Machine Language English Abstract from JPO of JP 58-225103 A.

Machine Language English Abstract and Translation from JPO of JP 2013-8951 A, which is equivalent to WO 2012/161106 A1.

Joona Bang et al., "Facile Routes to Patterned Surface Neutralization Layers for Block Copolymer Lithography", Advanced Materials vol. 19, pp. 4552-pp. 4557 (2007).

Christopher N. Bates et al., "Single- and Dual-Component Cross-Linked Polymeric Surface Treatments for Controlling Block Copolymer Orientation", Polymer Preprints vol. 52(1), pp. 181-pp. 182 (2011).

Kenneth C. Caster, "Applications of Polymer Brushes and Other Surface-Attached Polymers", Polymer Brushes Part 17, pp. 331-370 (2004).

Eric Drockenmuller et al., "Covalent Stabilization of Nanostructures: Robust Block Copolymer Templates from Novel Thermoreactive Systems," Journal of Polymer Science: Part A: Polymer Chemistry, vol. 43, pp. 1028-pp. 1037 (2005).

Iain E. Dunlop, "Interactions Between Polymer Brushes: Varying the Number of End-Attaching Groups", Macromol, Chem. Phys. vol. 205, pp. 2443-pp. 2450 (2004).

Eungnak Han et al., "Photopatternable Imaging Layers for Controlling Block Copolymer Microdomain Orientation", Advanced Materials vol. 19, pp. 4448-pp. 4452 (2007).

Craig J. Hawker et al., "Facile Synthesis of Block Copolymers for Nanolithographic Applications", Polymer Preprints vol. 46(2), pp. 239-pp. 240 (2005).

Craig J. Hawker, Initiating Systems for Nitroxide-Mediated "Living" Free Radical Polymerizations: Synthesis and Evaluation, Macromolecules vol. 29 No. 16, pp. 5245-pp. 5254, published 1996.

Atsushi Hieno et al., "Quick Formation of DSA Neutralization Polymer Layer Attached by Reactive Self-Assembled Monolayer," J. Photopol. Sci. Tech. vol. 25 No. 1, pp. 73-pp. 76 (2012).

E. Huang et al., "Using Surface Active Random Copolymers to Control the Domain Orientation in Diblock Copolymer Thin Films", Macromolecules vol. 31 No. 22, pp. 7641-pp. 7650 (1998).

Shengxiang Ji et al., "Preparation of Neutral Wetting Brushes for Block Copolymer Films from Homopolymer Blends", Advanced Materials vol. 20, pp. 3054-pp. 3060 (2008).

G. J. Kellogg et al., "Observed Surface Energy Effects in Confined Diblock Copolymers", Physical Review Letters vol. 76 No. 14, pp. 2503-pp. 2506 (1996).

Bokyung Kim et al., "Dewetting of PMMA on PS-Brush Substrates", Macromolecules vol. 42 No. 20, pp. 7919-pp. 7923 (2009).

Bong Hoon Kim et al.; The Synthesis of Randum Brush for Nanostructure of Block Copolymer, Macromol. Symp., vol. 249-250, pp. 303-pp. 306 (2007).

Bumjoon J. Kim et al., "Importance of End-Group Structure in Controlling the Interfacial Activity of Polymer-Coated Nanoparticles", Macromolecules vol. 40 No. 6, pp. 1796-pp. 1798 (2007).

Yoojin Kim et al., "Effect of Architecture on the Self-Assembly of Block Copolymers at Interfaces: Linear-nanoparticle vs. Linear AB Diblocks", Polymeric Materials: Science & Engineering Vo. 92, pp. 399-pp. 400 (2005).

Yoojin Kim et al., "The Dramatic Effect of Architecture on the Self-Assembly of Block Copolymers at Interfaces", Langmuir vol. 21 No. 23, pp. 10444-pp. 10458 (2005).

Massimo Lazzari et al., "Methods for the Alignment and the Large-scale Ordering of Block Copolymer Morphologies," Block Copolymers in Nanoscience, Edited by M. Lazzari, G. Liu, and S. Lecommandoux, Copyright © 2006 WILEY-VCH Verlag GmbH & Co. KGaA, Weinheim, pp. 191-pp. 231.

Julie M. Leiston-Belanger et al., "A Thermal and Manufacture Approach to Stabilized Diblock Copolymer Templates", Macromolecules vol. 38 No. 18, pp. 7676-pp. 7683 (2005).

Mao-Peng Lin et al., "Photocrosslinking of Polymers Containing Cationically Polymerizable Groups in the Side-Chain by Sulfonium Salts," Journal of Polymer Science Part A: Polymer Chemistry vol. 30 Issue 5, pp. 933-pp. 936, (1992).

Nancy A. Listigovers et al., "Narrow Polydispersity Diblock and Triblock Copolymers of Alkyl Acrylates by a "Living" Stable Free Radical Polymerization", Macromolecules vol. 29 No. 27, pp. 8992-pp. 8993 (1996).

Hui Liu et al., "Random Poly(methyl methacrylate-*co*-styrene) Brushes by ATRP to Create Neutral Surfaces for Block Copolymer Self-Assembly," Macromol. Chem. Phys. vol. 213, pp. 108-pp. 115 (2012).

P. Mansky et al., "Controlling Polymer-Surface Interactions with Random Copolymer Brushes", Science Magazine vol. 275, pp. 1458-pp. 1460 (1997).

Holger Merlitz, "Surface Instabilities of Monodisperse and Densely Grafter Polymer Brushes", Macromolecules vol. 41 No. 13, pp. 5070-pp. 5072 (2008).

Hironobu Murata et al., "Synthesis of Functionalized Polymer Monolayers from Active Ester Brushes", Macromolecules vol. 40 No. 15, pp. 5497-pp. 5503 (2007).

Timothy E. Patten et al., "Atom Transfer Radical Polymerization and the Synthesis of Polymeric Materials", Adv. Mater. vol. 10 Issue 12, pp. 901-pp. 915 (1998).

R. P. Quirk et al., "Thermoplastic Elastomers 2nd Edition", Hanser/Gardner Publications, pp. 74-pp. 78 (1996).

Ricardo Ruiz et al., "Density Multiplication and Improved Lithography by Directed Block Copolymer Assembly", Science Magazine vol. 321, pp. 936-pp. 939 (2008.

Du Yeol Ryu et al., "Cylindrical Microdomain Orientation of PS-*b*-PMMA on the Balanced Interfacial Interactions: Composition Effect of Block Copolymers," Macromolecules vol. 42 No. 13, pp. 4902-pp. 4906 (2009).

Du Yeol Ryu et al., "A Generalized Approach to the Modification of Solid Surfaces", Science Magazine vol. 308, pp. 236-pp. 239 (2005).

Toru Yamaguchi et al., "Resist-Pattern Guided Self-Assembly of Symmetric Diblock Copolymer", Journal of Photopolymer Science and Technology vol. 19 No. 3, pp. 385-pp. 388 (2006).

Toru Yamaguchi et al., "Two-Dimentional Patterning of Flexible Designs with High Half-Pitch Resolution by Using Block Copolymer Lithography", Advanced Materials vol. 20, pp. 1684-pp. 1689 (2008).

Yuanlie Yu et al., "The synthesis of novel fluorine-containing random polymer and application in modification of solid surfaces", Surface & Coatings Technology vol. 205, pp. 295-pp. 212 (2010.

Form PCT/ISA/220, Form PCT/ISA/210, and Form PCT/ISA/237 dated Feb. 26, 2013 for PCT/IB2012/001905, which corresponds to U.S. Appl. No. 13/243,640.

Form PCT/IB/326, Form PCT/IB/373, and Form PCT/ISA/237 dated Apr. 3, 2014 for PCT/IB2012/001905, which corresponds to U.S. Appl. No. 13/243,640.

\* cited by examiner

NEUTRAL LAYER POLYMER COMPOSITION FOR DIRECTED SELF ASSEMBLY AND PROCESSES THEREOF

The present application for patent is in the field of lithographic patterning by directed self assembly and more specifically in the area of neutral underlayers that support the formation of lithographically patterned features.

In recent years, directed self assembly has emerged as a useful means of organizing self-assembled nanostructures deposited from solution to create lithographic features and for a wide variety of other applications. For example, see Thurn-Albrecht et al., "Ultrahigh Nanowire Arrays Grown in Self-Assembled. Diblock Copolymer Templates", Science, 290, 2126, (2000); Black et al., "Integration of Self-Assembled Diblock Copolymers for Semiconductor Capacitor Fabrication," Applied Physics Letters, 79, 409, (2001) and Akasawa et al., "Nanopatterning with Microdomains of Block Copolymers for Semiconductor Capacitor Fabrication," Jpn. J. Appl. Phys., 41, 6112, (2002).

In many directed self assembly applications, molecular interactions drive phase separation of various portions of the self assembly material into domains; wherein immiscible polar and non-polar regions of the self assembly materials become concentrated. Of particular interest in directed self assembly applications are thin films of block copolymers that have polar and non-polar blocks with predetermined sizes. These blocks of selected size provide selected domains of a length associated with their respective molecular weights and compositions. Further, by tuning the molar masses of the individual blocks within the block copolymers, one can generate various morphologies with selected sizes, such as lamellae or cylinders of a specific width, specific pitch and specific symmetry patterns such as hexagonal close packed arrays or parallel lines.

Film layers made with energy neutral polymers (hereinafter called neutral layers) are sometimes used as underlayers for self assembling polymers because they have a uniform surface energy. A non-uniform surface energy might interfere with the assembling process by the block polymer as one of the blocks may show a preferred attraction to the film layer over another block. Thus neutral layers tend not to enforce or guide, preferentially, the formation of a particular domain of the self assembling block copolymer at a particular location. Neutral layers may be functionalized polymer brush copolymers, cross-linkable polymers, random copolymers having similar repeat units to those used in the block copolymer being used, or blends of homo-polymers, each respectively having similar monomers to those in the block copolymer being used.

Among the methods used to guide self-assembly in thin films of block copolymers are graphoepitaxy and chemical epitaxy. In graphoepitaxy self-assembly is guided by the pre-formed topographical structures such as trenches. For example, a topographically patterned substrate with a neutral underlying surface and with sidewalls that are preferentially attracted to one type of the block copolymer domain (for example, the A domains of an A-B diblock copolymer assembly) can be used to direct self-assembly inside the trench through topographical confinement. With a trench of width L and a block copolymer (BCP) having a periodicity of $P_{BCP}$ frequency multiplication of a factor of $L/P_{BCP}$ can be achieved for the remaining domain.

Neutral layers may be formed from random brush copolymers, end substituted with reactive functional groups that are capable of attaching to the surface of a particular substrate. To provide the greatest degree of energy neutrality, it is desired that the reactive functional group on the random copolymer is provided at or near at least one end of the polymer chain so that the energy neutral portion of the random copolymer can be presented to the desired block copolymer being applied to it.

Various attempts have been made to incorporate functional groups near the end of the random copolymer chain as described supra. For example, Colburn et al. in U.S. Pat. No. 8,017,194 disclose the synthesis of a random styrene-methylmethacrylate copolymer with a reactive benzyl alcohol end group prepared by nitroxide-mediated free radical polymerization, wherein the nitroxide is functionalized. However, functionalized nitroxide initiators are difficult to scale up and expensive, resulting in considerably higher cost for the copolymer. Moreover, nitroxide mediated polymerization is carried out at high temperature, leading to considerable autopolymerization of the monomers, thus resulting in an undesirable concentration of polymer chains without the desired end groups.

Therefore, there remains a need for polymers that are synthesized at low temperature by methods that incorporate the desired reactive end groups reliably and at reduced cost.

SUMMARY OF THE INVENTION

The present invention relates to a novel polymeric composition comprising a polymer comprising a) two or more repeat units and b) a terminus having the structure 1)

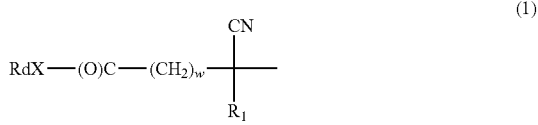

wherein $R_1$ represents a $C_1$-$C_{20}$ substituted or unsubstituted alkyl group, w is a number from 1-8, X is O or N and $R_d$ is at least one group chosen from i) to viii) from Table 1. The invention also relates to a process for forming a pattern using the novel polymeric composition. The invention further relates to a process of making the novel polymer.

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive. Further, the conjunction "or" is understood to be exclusive when describing chemical substitution on a single site. The articles "a" and "the" as used herein are understood to encompass the plural as well as the singular.

As used herein, the term "copolymer" is understood to comprise two or more monomer repeat units and the term "polymer" may be a homopolymer or a copolymer.

As used herein, when referring to alkylene, alkenylene or arylene groups and functionalities, it is to be understood that heteroatoms may or may not form part of the chain, such as, for example, oxygen atoms, substituted or unsubstituted nitrogen atoms, sulfur atoms, substituted or unsubstituted silicon atoms and the like.

Disclosed and claimed herein is a novel polymeric composition comprising a novel polymer having two or more repeat units and a terminus having the structure 1):

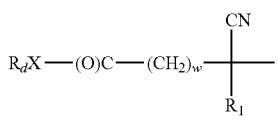 (1)

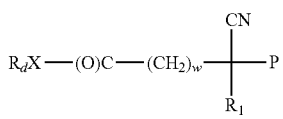 (1')

wherein $R_1$ represents a $C_1$-$C_{20}$ substituted or unsubstituted alkyl group, w is a number from 1-8, X is oxygen (O) or nitrogen (N), and $R_d$ is a group chosen from any one of the various reactive end groups i) to viii) as shown in Table 1. Herein in the present application, the terminus group of structure 1) is attached to the polymer, P, having two or more repeat units, as shown in structure 1'). When X=O, $R_d$ is a group chosen from at least one of the various reactive end groups i) to viii) as shown in Table 1. When X=N, $R_d$ is at least one or two of the reactive groups shown in Table 1. Herein where X is N, then there are two substituents attached to N referred to $R_d$. Therefore, in this embodiment, where X is N, $R_d$ comprises $R_d'$ and $R_d''$, and $R_d'$ and $R_d''$ can be selected independently from a group consisting of hydrogen, an alkyl having 1-20 carbon atoms, substituted alkyl group having 1-20 carbon atoms and at least one substituent group selected from groups i) to viii) as shown in Table 1. The repeat units of the polymer may be derived from any type of vinyl comonomers.

TABLE 1

| | | |
|---|---|---|
| i) | 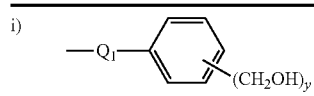 | where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; y = 1-5; |
| ii) | 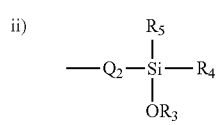 | where $Q_2$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms, $R_3$ represents hydrogen, an alkyl or substituted alkyl group having 1-20 carbon atoms, and $R_4$, and $R_5$ represent, independently, hydrogen or an alkyl or substituted alkyl group having 1-20 carbon atoms, or a hydroxy, alkoxy or substituted alkoxy group having 1-20 carbon atoms; |

TABLE 1-continued

| | | |
|---|---|---|
| iii) | 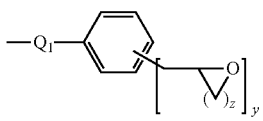 | where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; y = 1-5; |
| iv) |  —Ar—CH$_2$OH | where Ar represents a substituted or unsubstituted arylene group having 6 to 20 carbon atoms or a substituted or unsubstituted heteroarylene group having 5 to 20 carbon atoms; |
| v) | 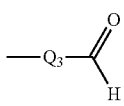 | where $Q_3$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; |
| vi) | 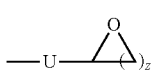 | where U represents a substituted or unsubstituted alkylene group having 1 to 20 carbon atoms; and z is 1-2; |
| vii) | 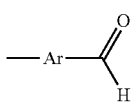 | where Ar represents a substituted or unsubstituted arylene group having 6 to 20 carbon atoms or a substituted or unsubstituted heteroarylene group having 5 to 20 carbon atoms. |
| viii) |  (RO)$_2$OP—(CH$_2$)$_w$— | where R represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms, and w is a number from 1-10. |

In one embodiment of the polymer, the terminus group of structure 1 is where X=O, and $R_d$ is a reactive group chosen from at least one of the reactive end groups i) to viii) as shown in Table 1. In another embodiment of the polymer, the terminus group of structure 1 is where X=O, and $R_d$ is a reactive group chosen from any one of the various reactive end groups i) to vii) as shown in Table 1. In another embodiment of the polymer, the terminus group of structure 1 is where X=N, and $R_d$ comprises $R_d'$ and $R_d''$, and $R_d'$ and $R_d''$ can be selected independently from a group consisting of hydrogen, an alkyl having 1-20 carbon atoms, substituted alkyl group having 1-20 carbon atoms and at least one substituent selected from groups i) to viii) as shown in Table 1.

In another embodiment of the polymer, the terminus group of structure 1) is where X=O, and $R_d$ is an interface reactive group chosen from any one of the various reactive end groups i) or ii) as shown in Table 1. Examples of $Q_1$ are $CH_2$, $CH_2CH_2$, $CH_2CH_2CH_2$, $CH_2CH_2CH_2CH_2$. Examples of $Q_2$ are $CH_2$, $CH_2CH_2$, $CH_2CH_2CH_2$, $CH_2CH_2CH_2CH_2$. Examples of $R_3$ are $CH_3$, $CH_2CH_3$, $CH_2CH_2CH_3$, $CH_2CH_2CH_2CH_3$, $C(CH_3)_3$. Examples of $R_4$ and $R_5$ are $CH_3$, $CH_2CH_3$, $CH_2CH_2CH_3$, $CH_2CH_2CH_2CH_3$, $C(CH_3)_3$, $OCH_3$, $OCH_2CH_3$, $OCH_2CH_2CH_3$, $OC(CH_3)_3$.

Specific examples of the terminus group of structure 1) are

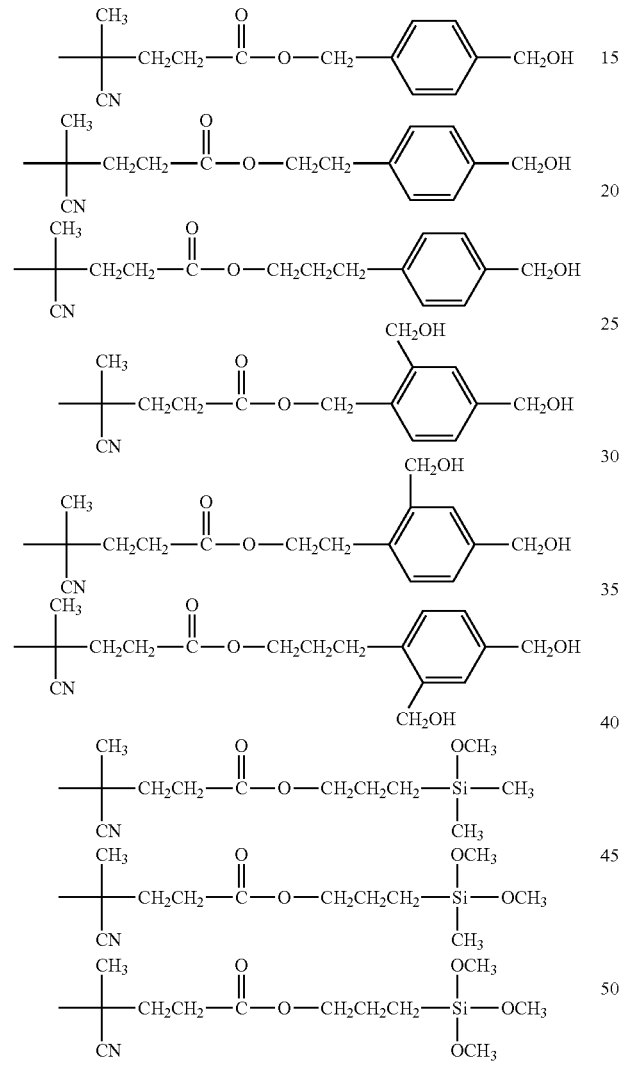

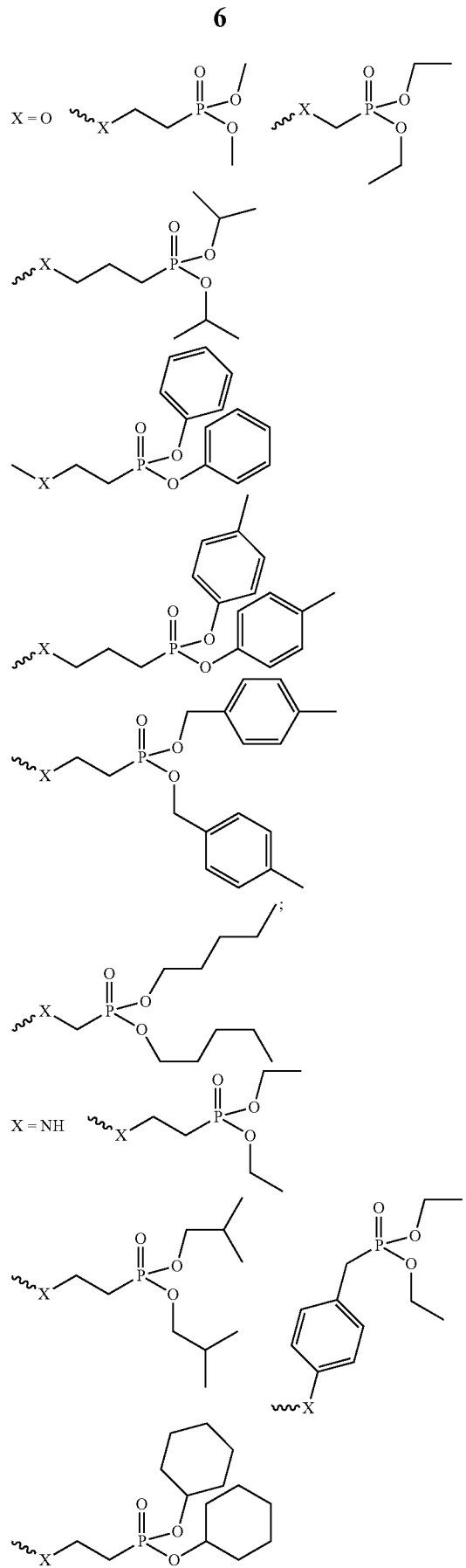

In another embodiment of the polymer the terminus group of structure 1) is where X=N, and $R_d$ comprises $R_d'$ and $R_d''$, and $R_d'$ and $R_d''$ can be selected independently from a group consisting of hydrogen, an alkyl having 1-20 carbon atoms, substituted alkyl group having 1-20 carbon atoms and at least one substituent selected from group viii) as shown in Table 1.

Examples of R are methyl, ethyl, propyl, isopropyl, butyl, isobutyl, tert-butyl, pentyl, iso-pentyl, hexyl, iso-hexyl, cyclohexyl, phenyl, o-methyl$C_6H_4$, m-methyl$C_6H_4$ p-methyl$C_6H_4$, PhCH$_2$; o-methyl$C_6H_4CH_2$, m-methyl$C_6H_4CH_2$, p-methyl$C_6H_4CH_2$, etc., and w may be 1, 3 or 4. Specific examples of the moiety viii) connected to O or NH are:

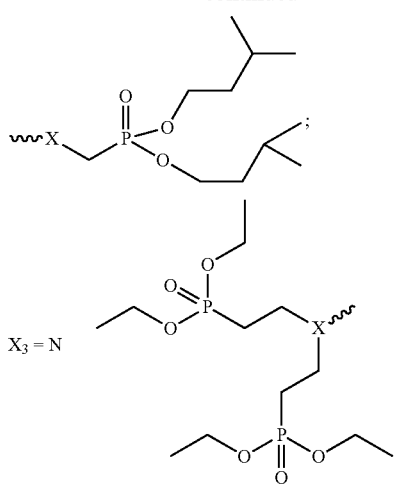

$X_3 = N$

Further disclosed and claimed herein is a polymeric composition, formed by a process comprising: (a) providing, to a reaction vessel, 4,4'-azobis(4-cyanovaleric acid) or a corresponding salt, wherein the salt comprises at least one quaternary cation; (b) providing one or more monomers to the reaction vessel to form a reactive mixture; (c) heating the reactive mixture at a temperature less than 100° C. or less than 90° C. for a time of 1-80 hours to form a polymer, then; (d) providing, to the resulting polymer, a halogenated compound, the halogenated compound chosen from materials shown in Table 2. Halogen compounds are any of fluorine, chlorine, bromine, iodine, etc.

TABLE 2

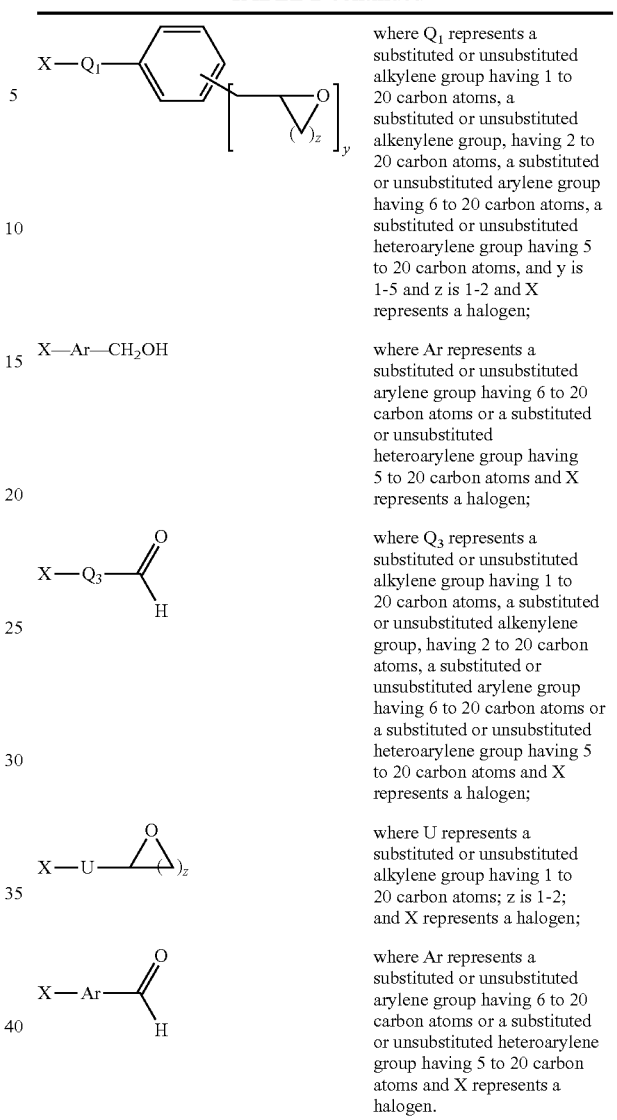

| | |
|---|---|
| $X\text{—}Q_1\text{—}\text{(phenyl)}(CH_2OH)_y$ | where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarytene group having 5 to 20 carbon atoms and X represents a halogen; y = 1-5; |
| 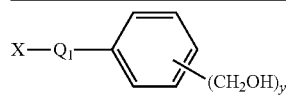 | where $Q_2$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms, $R_3$ represents hydrogen an alkyl or substituted alkyl group having 1-20 carbon atoms, and $R_4$, and $R_5$ represent, independently, hydrogen or an alkyl or substituted alkyl group having 1-20 carbon atoms, or a hydroxy, alkoxy or substituted alkoxy group having 1-20 carbon atoms and X represents a halogen; |

TABLE 2-continued

| | |
|---|---|
| $X\text{—}Q_1\text{—}\text{(phenyl)}[\text{(epoxide)}_z]_y$ | where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms, a substituted or unsubstituted heteroarylene group having 5 to 20 carbon atoms, and y is 1-5 and z is 1-2 and X represents a halogen; |
| $X\text{—}Ar\text{—}CH_2OH$ | where Ar represents a substituted or unsubstituted arylene group having 6 to 20 carbon atoms or a substituted or unsubstituted heteroarylene group having 5 to 20 carbon atoms and X represents a halogen; |
| $X\text{—}Q_3\text{—}CHO$ | where $Q_3$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms and X represents a halogen; |
| 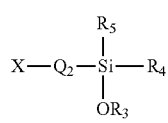 | where U represents a substituted or unsubstituted alkylene group having 1 to 20 carbon atoms; z is 1-2; and X represents a halogen; |
| $X\text{—}Ar\text{—}CHO$ | where Ar represents a substituted or unsubstituted arylene group having 6 to 20 carbon atoms or a substituted or unsubstituted heteroarylene group having 5 to 20 carbon atoms and X represents a halogen. |

In the above process, providing to a reaction vessel, a salt of 4,4'-azobis(4-cyanovaleric acid) is understood to include adding the purified salt or forming the salt in situ by adding the acid and then the corresponding quaternary ammonium hydroxide.

Further disclosed and claimed herein is a functionalized free radical initiator comprising: a compound having the structure

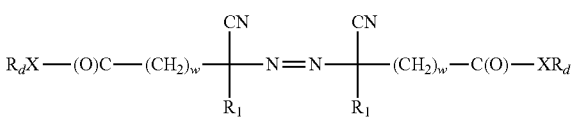

wherein $R_1$ represents a substituted or unsubstituted alkyl group having 1-20 carbon atoms, w is 1-8, X is O or N and $R_d$ is a reactive group. When X=O, $R_d$ is an reactive group chosen from the groups i) to viii) listed in Table 1, and when X=N, $R_d$ comprises $R_d'$ and $R_d''$, and $R_d'$ and $R_d''$ can be selected independently from a group consisting of hydrogen, an alkyl having 1-20 carbon atoms, substituted alkyl group having 1-20 carbon atoms and at least one substituent group selected from groups i) to viii) as shown in Table 1. In one embodiment the substituent group is at least one of (RO)$_2$OP—(CH$_2$)$_w$. In another embodiment the substituent group is at least one of the end selected from group i) and group ii).

The halogenated compound chosen from materials shown in Table 2 may be exemplified by

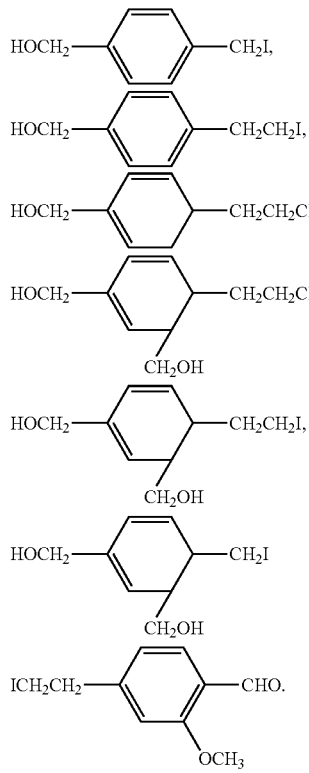

Further disclosed and claimed herein is a polymeric composition formed by a process comprising: (a) providing, to a reaction vessel, the functionalized free radical initiator described supra; (b) providing one or more monomers to the reaction vessel to form a reactive mixture; and heating the reactive mixture at a temperature less than 100° C. or less than 90° C. for a time of 1-80 hours. The polymer may be isolated and purified as is known. Monomers used for the polymerization may be those which comprise unsaturation such that free radical polymerization may take place, such as vinyl compounds; for example (meth)acrylates, styrenic monomers, etc.

The polymeric compositions, described supra may be polymers or copolymers whose monomer repeat units are described infra.

Further disclosed and claimed herein is a neutral layer formulation comprising any of the polymeric compositions described supra and a solvent. The neutral layer formulation may optionally comprise a thermal acid generator and/or a photoacid generator.

Suitable thermal acid generators include the onium salts, halogen containing compounds, perfluorobenzene sulfonate esters, perfluoroalkane sulfonate esters. Without limitation, exemplary thermal acid generators for the above formulation include tri-C$_1$-C$_8$-alkylammonium p-toluenesulfonate, tri-C$_1$-C$_8$-alkylammonium dedecylbenzenesulfonate, tri-C$_1$-C$_8$-alkylammonium perfluorobutane-1-sulfonate, tri-C$_1$-C$_8$-alkylammonium trifluoromethane-sulfonate, N-hydroxyphthalimide trifluoromethane-sulfonate, bis(4-t-butyl phenyl)iodonium trifluoromethane sulfonate, bis(4-t-butyl phenyl)iodonium perfluoro-1-butanesulfonate, bis(4-t-butyl phenyl)iodonium perfluoro-1-octanesulfonate, bis (phenyl)iodonium hexafluoroantimonate, N-hydroxy-5-norbornene-2,3-dicarboximide perfluoro-1-butanesulfonate, 2-nitrobenzyl trifluoromethanesulfonate, 4-nitrobenzyl trifluoromethanesulfonate, 2-nitrobenzyl perfluorobutane-sulfonate, 4-nitrobenzyl perfluorobutanesulfonate or a combination comprising at least one of the foregoing.

Suitable photoacid generators include, for example, aromatic and aliphatic sulfonium salts and iodonium salts.

Suitable solvents for the neutral layer formulation include glycol ether acetates, esters, hydroxy esters, alkoxy esters alcohols, ketones, amids, imindes, ethers, ether esters, ether alcohols and the like. Specifically, solvents may include, without limitation, propylene glycol monomethyl ether (PGME), ethylene glycol monoethyl ether acetate, propylene glycol monomethyl ether acetate (PGMEA), ethyl-3-ethoxypropionate, methyl-3-methoxypropionate, butyl acetate, amyl acetate, cyclohexyl acetate, 3-methoxybutyl acetate, 3-ethoxyethyl propionate, 3-ethoxymethyl propionate, 3-methoxymethyl propionate, methyl acetoacetate, ethyl acetoacetate, methyl pyruvate, ethyl pyruvate, propylene glycol monomethyl ether propionate, propylene glycol monoethyl ether propionate, methyl ethyl ketone, methyl amyl ketone, cyclohexanone, cyclopentanone, diacetone alcohol, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethylsulfoxide, γ-butyrolactone, propylene glycol methyl ether acetate, propylene glycol ethyl ether acetate, propylene glycol propyl ether acetate, methyl lactate, ethyl lactate (EL), propyl lactate, and tetramethylene sulfone. The solvents may be used alone or as mixtures.

The above formulation may further comprise suitable thermal curing agents that include, but are not limited to, imidazoles, primary, secondary, and tertiary amines, quaternary ammonium salts, anhydrides, polysulfides, polymercaptans, phenols, carboxylic acids, polyamides, quaternary phosphonium salts, and combinations thereof.

Without limitation the novel polymer having two or more repeat units and a terminus are novel copolymers described and claimed herein may comprise one or more monomer repeat units chosen from styrene, methyl(meth)acrylate, butadiene, butyl(meth)acrylate, vinylpyridine, isoprene, hexyl(meth)acrylate, isobutylene, ethylene, 2-butylstyrene, 3-butylstyrene, 4-butylstyrene, 3-(trimethoxysilyl)propyl (meth)acrylate, 3-(triethoxysilyl)propyl(meth)acrylate, glycidyl(meth)acrylate, pentaerythritol tri(meth)acrylate, oxetan-2-ylmethyl(meth)acrylate and similar monomers.

Polymers that are reacted to form the polymer with the terminus group above, and described and claimed herein may be copolymers. Without limitation, copolymers that are reacted may comprise poly(methylmethacrylate-styrene) poly(butadiene-butylmethcrylate), poly(butadiene-dimethylsiloxane), poly(butadiene-methylmethacrylate), poly(butadiene-vinylpyridine), poly(isoprene-methylmethacrylate), (polyisoprene-vinylpyridine), poly(butylacrylate-methylmethacrylate), poly(butylacrylate-vinylpyridine), (polyhexylacrylate-vinylpyridine), poly(isobutylene-butylmethacrylate), poly(isobutylene-dimethoxysiloxane), polyisobutylene-methylmethacrylate), poly(isobutylene-vinylpyridine), poly(isoprene-ethyleneoxide), poly(butylmethacrylate-butylacrylate), poly(butylmethacrylate-vinylpyridine), poly(ethylene-methylmethacrylate), poly (methylmethacrylate-butylacrylate), poly(methylmethacrylate-butylmethacrylate), poly(styrene-butadiene), poly(styrene-butylacrylate), poly(styrene-butylmethacrylate), poly(styrene-butylstyrene), poly(styrene-dimethoxysiloxane), polystyrene-isoprene), poly(styrene-methylmethacrylate), poly(styrene-vinylpyridine), poly(ethylene-vinylpyridine), poly(vinylpyridine-methylmethacrylate), poly(ethyleneoxide-isoprene), poly(ethyleneoxide-butadiene), poly(ethyleneoxide-styrene), or poly(ethyleneoxide-methylmethacrylate).

The novel neutral polymer layer composition is coated on any desired substrate and heated to remove the solvent from the film. The heating can range from about 100° C. to about 300° C., or about 150° C. to about 300° C. The film thickness after coating can range from 3 to about 500 nm or thicker. Optionally, after coating and baking, an additional solvent step may be added to reduce the film thickness to form a thin grafted layer which remains attached to the substrate, which can range from about 3 nm to about 50 nm after heating, or about 3 nm to about 30 nm, or about 3 nm to about 25 nm, or about 3 nm to about 20 nm, or about 3 nm to about 10 nm. Any solvents capable of dissolving the brush polymer may be used to reduce the film. Optionally, the film can be heated further after thinning at temperatures ranging from about 80° C. to about 150° C., or from about 90° C. to about 140° C. Once the novel polymer film has been formed the coating may be used for further processing to finally form a pattern using any self directed assembly techniques. The composition used for forming a layer over the novel neutral layer comprises a block copolymer and a solvent. Examples of such techniques are graphoepitaxy, standard chemoepitaxy, chemoepitaxy with pinning, etc. The thin grafted neutral layers formed by the novel neutral layer composition remain neutral and attached to the substrate despite any damage that might occur during the lithographic processes where the neutral layer is used, such as dissolution from organic solvents (such as solvents used to form coatings above the neutral layer, solvent developers, etc), dissolution in aqueous alkaline developers, damage from processes used to image the photoresist coated over the neutral layer (such as e-beam, euv, deep uv, etc), or dissolution in photoresist strippers. The thinned brush layers are not removable in solvents such as those that are used to coat the photoresist, such as PGMEA, PGME, EL, etc. Over the novel neutral layer, a block copolymer composition useful for directed self assembly is used to form a layer.

The block copolymer for use in directed self assembly in conjunction with the novel neutral layer composition can be any block copolymers which can form domains through self assembly. The microdomains are formed by blocks of the same type which tend to self associate. Typically, block copolymer employed for this purpose are polymers in which the repeat units derived from monomers are arranged in blocks which are different compositionally, structurally or both and are capable of phase separating and forming domains. The blocks have differing properties which can be used to remove one block while keeping the other block intact on the surface, thus providing a pattern on the surface. Thus, the block may be selectively removed by plasma etching, solvent etching, developer etching using aqueous alkaline solution, etc. In block copolymers based on organic monomers, one block can be made from polyolefinic monomers including polydienes, polyethers including poly(alkylene oxides) such as polyethylene oxide), polypropylene oxide), poly(butylene oxide) or mixtures thereof; and, the other block can be made from different monomers including poly((meth) acrylates), polystyrenes, polyesters, polyorganosiloxanes, polyorganogermanes, and or mixtures thereof. These blocks in a polymer chain can each comprise one or more repeat units derived from monomers. Depending on the type of pattern needed and methods used different types of block copolymers may be used. For instance, these may consist of diblock copolymers, triblock copolymers, terpolymers, or multiblock copolymers. The blocks of these block copolymers may themselves consist of homopolymers or copolymers. Block copolymers of different types may also be employed for self assembly, such as dendritic block copolymers, hyper-branched block copolymers, graft block copolymers, organic diblock copolymers, organic multiblock copolymers, linear block copolymers, star block copolymers amphiphilic inorganic block copolymers, amphiphilic organic block copolymers or a mixture consisting of at least block copolymers of different types.

The blocks of organic block copolymer may comprise repeat units derived from monomers such as $C_{2-30}$ olefins, (meth)acrylate monomers derived from $C_{1-30}$ alcohols, inorganic-containing monomers including those based on Si, Ge, Ti, Fe, Al. Monomers based on $C_{2-30}$ olefins can make up a block of high etch resistance alone or do so in combination with one other olefinic monomer. Specific example of olefinic monomers of this type are ethylene, propylene, 1-butene, 1,3-butadiene, isoprene, dihydropyran, norbornene, maleic anhydride, styrene, 4-hydroxy styrene, 4-acetoxy styrene, 4-methylstyrene, alpha-methylstyrene or mixtures thereof. Examples of highly etchable units can be derived from (meth) acrylate monomers such as (meth)acrylate, methyl(meth) acrylate, ethyl(meth)acrylate, n-propyl(meth)acrylate, isopropyl(meth)acrylate, n-butyl(meth)acrylate, isobutyl(meth) acrylate, n-pentyl(meth)acrylate, isopentyl(meth)acrylate, neopentyl(meth)acrylate, n-hexyl(meth)acrylate, cyclohexyl (meth)acrylate, isobornyl(meth)acrylate, hydroxyethyl (meth)acrylate or mixtures thereof.

An illustrative example of a block copolymer containing one type of high etch resistant repeat unit would be a polystyrene block containing only repeat units derived from styrene and another type of highly etchable polymethylmethacrylate block containing only repeat units derived from methylmethacrylate. These together would form the block copolymer poly(styrene-b-methylmethacrylate), where b refers to block.

Specific non-limiting examples of block copolymers that are useful for graphoepitaxy, chemoepitaxy or pinned chemoepitaxy as used for directed self assembly on a patterned neutral layer, are poly(styrene-b-vinyl pyridine), poly(styrene-b-butadiene), poly(styrene-b-isoprene), poly(styrene-b-methyl methacrylate), poly(styrene-b-alkenyl aromatics), poly(isoprene-b-ethylene oxide), poly(styrene-b-(ethylene-propylene)), poly(ethylene oxide-b-caprolactone), poly(butadiene-b-ethylene oxide), poly(styrene-b-t-butyl (meth)acrylate), poly(methyl methacrylate-b-t-butyl methacrylate), poly(ethylene oxide-b-propylene oxide), poly(styrene-b-tetrahydrofuran), poly(styrene-b-isoprene-b-ethylene oxide), poly(styrene-b-dimethylsiloxane), poly(methyl methacrylate-b-dimethylsiloxane), or a combination comprising at least one of the above described block copolymers. All these polymeric materials share in common the presence of at least one block which is rich in repeat units resistant to etching techniques typically employed in manufacturing IC devices and at least one block which etches rapidly under these same conditions. This allows for the directed self assembled polymer to pattern transfer onto the substrate to affect either pattern rectification or pattern multiplication.

Typically, the block copolymers employed for the directed self assembly such as in graphoepitaxy, chemoepitaxy or pinned chemoepitaxy have a weight-averaged molecular weight ($M_w$) in the range of about 3,000 to about 500,000 g/mol and a number averaged molecular weight ($M_n$) of about 1,000 to about 60,000 and a polydispersity ($M_w/M_n$) of about 1.01 to about 6, or 1.01 to about 2 or 1.01 to about 1.5. Molecular weight, both $M_w$ and $M_n$, can be determined by, for example, gel permeation chromatography using a universal calibration method, calibrated to polystyrene standards. This ensures that the polymer blocks have enough mobility to undergo self assembly when applied to a given surface either spontaneously, or by using a purely thermal treatment, or through a thermal process which is assisted by the absorption of solvent vapor into the polymer framework to increase flow of segments enabling self assembly to occur.

Solvents suitable for dissolving block copolymers for forming a film can vary with the solubility requirements of the block copolymer. Examples of solvents for the block copolymer assembly include propylene glycol monomethyl ether acetate (PGMEA), ethoxyethyl propionate, anisole, ethyl lactate, 2-heptanone, cyclohexanone, amyl acetate, n-butyl acetate, n-amyl ketone (MAK), gamma-butyrolactone (GBL), toluene, and the like. In an embodiment, specifically useful casting solvents include propylene glycol monomethyl ether acetate (PGMEA), gamma-butyrolactone (GBL), or a combination of these solvents.

The block copolymer composition can comprise additional components and/or additives selected from the group consisting of: inorganic-containing polymers; additives including small molecules, inorganic-containing molecules, surfactants, photoacid generators, thermal acid generators, quenchers, hardeners, cross-linkers, chain extenders, and the like; and combinations comprising at least one of the foregoing, wherein one or more of the additional components and/or additives co-assemble with the block copolymer to form the block copolymer assembly.

The substrate over which the novel neutral brush layer is formed may be any type of useful substrate. The substrate may have a pattern or be flat and unpatterned. A substrate that is patterned may use the processes described in and incorporated herein by reference by U.S. Ser. No. 13/243,640, filed Sep. 23, 2011, US 2009/0196488 filed Dec. 17, 2007, US 2008/0299353 filed Nov. 22, 2004, US 2010/0124629 filed Nov. 19, 2008, US 2009/0179002 filed Jan. 14, 2008 and U.S. Pat. No. 7,846,502, where the neutral layer used is the layer formed from the present novel composition. The novel brush polymer layer is formed prior to the step that requires a block copolymer layer useful for directed self assembly.

The block copolymer composition is applied over the novel neutral layer. The neutral layer may be formed on a patterned surface, where the pattern has been formed by conventional lithography, and where the neutral surface is a coating formed from the novel composition. Upon application and solvent removal, the block copolymer then undergoes self assembly directed by the specific pattern formed by conventional lithographic processing with the neutral layer through either actual topographical features or a patterned chemical difference of the substrate surface created by conventional lithographic process. Either pattern rectification maintaining the same resolution is achieved and/or pattern multiplication may also be achieved if multiple phase boundaries are formed between the features defined with conventional lithography, depending on the relative pitch of the pattern versus the microphase separation distance after standard IC processing to pattern transfer.

The application of the block copolymer by spinning techniques (including spin drying) can suffice to form the self directed block copolymer assembly. Other methods of self directed domain formation can occur during applying, baking, annealing, or during a combination of one or more of these operations. In this way, an oriented block copolymer assembly is prepared by the above method, having microphase-separated domains that comprise cylindrical microdomains oriented perpendicular to the neutral surface, or that comprise lamellar domains oriented perpendicular to the neutral surface. Generally, the microphase-separated domains are lamellar domains oriented perpendicular to the neutral surface, which provide parallel line/space patterns in the block copolymer assembly. The domains, so oriented, are desirably thermally stable under further processing conditions. Thus, after coating a layer of a block copolymer assembly including a useful diblock copolymer such as, for example, poly(styrene-b-methyl methacrylate), and optionally baking and/or annealing, the domains of the block copolymer will form on and remain perpendicular to the neutral surface, giving highly resistant and highly etchable regions on the surface of the substrate, which can be further pattern transferred in the substrate layers. The directed self assembled block copolymer pattern is transferred into the underlying substrate using known techniques. In one example wet etching or plasma etching could be used with optional UV exposure. Wet etching could be with acetic acid. Standard plasma etch process, such as a plasma comprising oxygen may be used; additionally argon, carbon monoxide, carbon dioxide, $CF_4$, $CHF_3$, may be present in the plasma.

In one embodiment of the present invention the initial photoresist patterned substrate used for forming the directed self assembly pattern can be defined using either negative or positive photoresists, or either positive tone or negative tone development processes, and imageable using any conventional lithographic techniques, such as e-beam, ion beam, x-ray, EUV (13.5 nm), broadband, or UV (450 nm-10 nm) exposure, immersion lithography, etc. In one embodiment the present invention is particularly useful for 193 nm imagewise exposure using either dry lithography or immersion lithography. For 193 nm lithography a commercially available positive 193 nm photoresist can be employed such as the non-limiting example of AZ AX2110P (available from AZ Electronic Materials USA Corp, Somerville, N.J.), photoresist from Shin-Etsu Chemical Corp., JSR Micro from Japan Synthetic Rubber, and other photoresists available from Fuji-Film, TOK, etc. These photoresists may be developed after exposure, and post exposure baked using an aqueous alkaline developer comprising tetramethylammonium hydroxide to give a positive tone pattern or developed using an organic solvent such as n-amyl ketone (MAK), n-butyl acetate, anisole, etc. to give a negative tone pattern. Alternatively, also for 193 nm exposure, commercially available negative tone photoresists may be employed. Once the pattern has been formed, a layer using the novel neutral layer composition is used to form a layer, and over this layer a layer of the self directed block copolymer is formed. The novel neutral film still retains neutrality thus allowing for proper orientation of the block copolymer domains between the topographical lithographic features. The neutrality is required to control the orientation of the block copolymer during the alignment process, such that the domains of the block copolymer will form on and remain perpendicular to the neutral surface.

The substrate over which the neutral layer is coated is any required by the device. In one example the substrate is a wafer coated with a layer of high carbon content organic layer with a coating of silicon or titanium containing antireflective coating, ARC, (high etch resistance to oxygen plasma) over it, which allows pattern transfer of the patterned block copolymer into these coatings. Suitable substrates include, without limitation, silicon, silicon substrate coated with a metal surface, copper coated silicon wafer, copper, aluminum, polymeric resins, silicon dioxide, metals, doped silicon dioxide, silicon nitride, silicon carbide, tantalum, polysilicon, ceramics, aluminum/copper mixtures, glass, coated glass; gallium arsenide and other such Group 111N compounds. These substrates may be coated with antireflective coating(s). The substrate may comprise any number of layers made from the materials described above. The substrate may be patterned or unpatterned.

For the present invention a variety of processes involving graphoepitaxy or (pinned) chemoepitaxy may be employed to achieve a directed self assembly of the aforementioned block copolymer using the novel neutral layer which is resistant to lithographic processes as described above, especially maintaining neutrality to control the orientation of the block copolymers relative to the substrate; this directed self assembly block copolymer coating is then used to form a high resolution pattern using plasma or wet etching to remove the highly etchable domains of the block copolymer. This pattern can then be further transferred into the substrate. In this manner, a variety of high resolution features may be pattern transferred into the substrate achieving either pattern rectification, pattern multiplication or both.

The above processes describe novel processes that can be practiced. The process can use the novel neutral layer composition of the present invention.

Each of the documents referred to above are incorporated herein by reference in its entirety, for all purposes. The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLES

Synthesis Example 1

(1) A solution was prepared by dissolving with stirring 5.0 g of 4,4'-azobis(4-cyanovaleric acid) in about 100 mL of methanol. To this was added slowly with stirring a solution consisting of an equimolar amount of tetramethylammonium hydroxide pentahydrate in methanol; stirring was continued for 30 min after the addition was complete. The solution was then concentrated at room temperature with a rotary-evaporator, and the residue poured into diethyl ether which upon stirring yielded a viscous oil. The oil was turned into a white solid by stirring it in a mixture of diethyl ether and acetone. Drying at room temperature yielded 5.5 g of the ammonium salt of 4,4'-azobis(4-cyanovaleric acid).
(2) A solution was prepared by dissolving 4 g of 4-(chloromethyl)benzyl alcohol in 30 ml of acetone. To this solution was added 5.7 g of sodium iodide dissolved in 25 g acetone. The mixture was stirred at room temperature for 17 hrs. The formed sodium chloride was filtered out. The filtrate was then concentrated to low volume using a rotary evaporator and poured into stirred DI water. The white solid obtained was isolated, washed thoroughly with deionized (DI) water and dried in a vacuum oven. Yield: 5 g of 4-(iodomethyl)benzyl alcohol.
(3) A solution was prepared by dissolving 4.9 g of 4-(iodomethyl)benzyl alcohol obtained in step (2) in 11 g dimethyl sulfoxide (DMSO). To this solution was added 4.3 g of the ammonium salt prepared in step (1) dissolved in 100 g of DMSO. The reaction mixture was stirred at room temperature for 18 hours. Tetramethylammonium iodide was filtered off to yield a filtrate. The filtrate was poured into DI water under stirring. The formed solid was filtered, washed thoroughly with water, and dried at room temperature giving 4 g of azo initiator with 2 benzyl alcohol groups, (E)-bis(4-hydroxyphenyl) 4,4'-(diazene-1,2-diyl)bis(4-cyanopentanoate).

Synthesis Example 2

A solution was prepared with 0.3023 g of the azo initiator (E)-bis(4-hydroxyphenyl) 4,4'-(diazene-1,2-diyl)bis(4-cyanopentanoate) prepared in Synthesis Example 1, 3.51 g of styrene and 2.47 g of methyl methacrylate dissolved in 14 g of 2-butanone in a 100 ml flask, equipped with a magnetic stirring bar and cold water condenser. After a nitrogen purge for 30 minutes, the flask was immersed in an 80° C. oil bath. The polymerization reaction was carried out with stirring at this temperature for 16 hrs. The reaction solution was then allowed to cool to room temperature. This solution was precipitated into methanol and the crude polymer isolated by filtration. The crude polymer was purified and isolated by first dissolving it into acetone and re-precipitating it in methanol, and then filtering off the polymer. The isolated polymer was dried in a 50° C. vacuum oven until constant weight (3 g). The polymer was found to have a weight average molecular weight (Mw) of 18810 g/mol and a number average molecular weight (Mn) of 11814 g/mol. $^1$H NMR showed the polymer contained 56.7 mol % styrene and 43.3 mol % MMA. Characteristic proton peaks assigned to benzyl alcohol end groups (4.6, 5.1 and 7.3 ppm) were clearly seen and estimated Mn based on proton NMR was in good agreement with Mn obtained from Gel Permeation Chromatography.

Synthesis Example 3

A solution was prepared with 0.70 g of the azo initiator (E)-bis(4-hydroxyphenyl) 4,4'-(diazene-1,2-diyl)bis(4-cyanopentanoate) prepared in Synthesis Example 1, 20.75 g of styrene and 7.0 g of methyl methacrylate dissolved in 42 g of 2-butanone in a 300 mL flask, equipped with a magnetic bar and cold water condenser. After a nitrogen purge for 30 min, the flask was immersed in an 80° C. oil bath. The polymerization reaction was carried out at this temperature for 21 hrs. The reaction solution was then allowed to cool to room temperature and precipitated into methanol. The crude polymer was isolated by filtration, and then purified and isolated by first dissolving it into acetone/2-butanone, re-precipitated with methanol and filtered. Finally the isolated polymer was dried in a 50° C. vacuum oven until constant weight (15 g) was obtained. The polymer was found to have an $M_w$ of 28648 g/mol and an $M_n$ of 17614 g/mol. $^1$H NMR showed that the polymer contained 71.8 mol % styrene and 28.2 mol % MMA. Characteristic proton peaks assigned to benzyl alcohol end groups (4.6, 5.1 and 7.3 ppm) were clearly seen and estimated Mn based on proton NMR was in good agreement with Mn obtained from GPC.

Synthesis Example 4

A solution was prepared with 1.6 g of the azo initiator (E)-bis(4-hydroxyphenyl) 4,4'-(diazene-1,2-diyl)bis(4-cyanopentanoate) prepared in Synthesis Example 1 and 30.8 g of methyl methacrylate dissolved in 70 g of 2-butanone in a 250 ml flask, equipped with a magnetic bar and cold water condenser. After a nitrogen purge for 30 min, the flask was immersed in an 80° C. oil bath. The polymerization reaction was carried out at this temperature for 20 hrs. The reaction solution was then allowed to cool to room temperature. The resulting solution was precipitated into methanol and the crude polymer isolated by filtration. The crude polymer was purified by dissolving it into 2-butanone and then re-precipitated into methanol. Finally, the isolated polymer was dried in a 50° C. vacuum oven until constant weight (23 g) was obtained. The polymer was found to have an Mw of 25,353 g/mol and a $M_n$ of 16,989 g/mol. Characteristic proton peaks assigned to benzyl alcohol end groups (4.6, 5.1 and 7.3 ppm) were clearly seen and estimated Mn based on proton NMR was in good agreement with Mn obtained from GPC.

Synthesis Example 5

A solution was prepared with 1.43 g of the azo initiator (E)-bis(4-hydroxyphenyl) 4,4'-(diazene-1,2-diyl)bis(4-cyanopentanoate) prepared in Synthesis Example 1 and 28.6 g of styrene dissolved in 54 g of 2-butanone in a 250 ml flask, equipped with a magnetic bar and cold water condenser. After a nitrogen purge for 30 min, the flask was immersed in an 80° C. oil bath. The polymerization reaction was carried out at that temperature for 18 hours. The resulting solution was then allowed to cool to room temperature and was precipitated into methanol. The crude polymer was isolated by filtration and purified by dissolving it into 2-butanone and re-precipitating it with methanol. Finally, the isolated polymer was dried in a 50° C. vacuum oven until constant weight (16.4 g) was obtained. The polymer was found to have a $M_w$ of 15175 g/mol and a $M_n$ of 9783 g/mol. Characteristic proton peaks assigned to benzyl alcohol end groups (4.6, 5.1 and 7.3 ppm) were clearly seen and estimated Mn based on proton NMR was in good agreement with Mn obtained from GPC.

Synthesis Example 6

A solution was prepared with the tetramethylammonium salt of 4,4'-azobis(4cyanovaleric acid) (1.22 g) (prepared by the same method described in Step 1 of Synthesis Example 1), 22.0 g of styrene and 7.4 g of methyl methacrylate dissolved in 70 g of dimethylsulfoxide (DMSO) in a 250 ml flask, equipped with a magnetic bar and cold water condenser. After a nitrogen purge for 30 min, the flask was immersed in an 80° C. oil bath. The polymerization reaction was carried out at this temperature for 21 hours. The reaction solution was then allowed to cool to room temperature and the resultant slightly cloudy solution was turned clear by adding a small amount of 2-butanone. To this clear solution was added 2 g of (3-iodopropyl)trimethoxysilane. This solution was stirred at room temperature for 24 hours. The tetramethylammonium iodide which formed was filtered away. The resulting filtrate was then precipitated into methanol and the crude polymer was isolated by filtration, dissolved into 2-butanone and re-precipitated with methanol. Finally the polymer was isolated and dried in 50° C. vacuum oven until constant weight (8.7 g) was obtained. The polymer was found to have an $M_w$ of 36514 g/mol and an $M_n$ of 17959 g/mol. Characteristic proton peaks assigned to silane end group (0 ppm) was clearly seen and estimated Mn based on proton NMR was in good agreement with Mn obtained from GPC.

Synthesis Example 7

A solution was prepared with 1.64 g of the azo initiator (E)-bis(4-hydroxyphenyl) 4,4'-(diazene-1,2-diyl)bis(4-cyanopentanoate) using method described in Synthesis Example 1, 20.26 g of styrene and 7.17 g of methyl methacrylate dissolved in 62 g of 2-butanone in a 500 mL flask, equipped with a magnetic bar and cold water condenser. After a nitrogen purge for 30 min, the flask was immersed in an 80° C. oil bath. The polymerization reaction was carried out at this temperature for 22 hours. The reaction solution was then allowed to cool to room temperature and precipitated into methanol. The crude polymer was isolated by filtration, and then purified and isolated by first dissolving it into acetone/2-butanone, re-precipitated with methanol and filtered. Finally the isolated polymer was dried in a 50° C. vacuum oven until constant weight (about 15 g) was obtained. The polymer was found to have an $M_w$ of 15657 g/mol and an $M_n$ of 10371 g/mol. $^1$H NMR showed that the polymer contained 69 mol % styrene and 31 mol % MMA. Characteristic proton peaks assigned to benzyl alcohol end groups (4.6, 5.1 and 7.3 ppm) were clearly seen and estimated Mn based on proton NMR was in good agreement with Mn obtained from GPC.

Synthesis Example 8

A solution was prepared with 1.56 g of the azo initiator (E)-bis(4-hydroxyphenyl) 4,4'-(diazene-1,2-diyl)bis(4-cyanopentanoate) using method described in Synthesis Example 1, 20 g of styrene and 6.1 g of methyl methacrylate dissolved in 60 g of 2-butanone in a 300 mL flask, equipped with a magnetic bar and cold water condenser. After a nitrogen purge for 30 min, the flask was immersed in an 80° C. oil bath. The polymerization reaction was carried out at this temperature for 24 hrs. The reaction solution was then allowed to cool to room temperature and precipitated into methanol. The crude polymer was isolated by filtration, and then purified and isolated by first dissolving it into acetone/2-butanone, re-precipitated with methanol and filtered. Finally the isolated polymer was dried in a 50° C. vacuum oven until constant weight (about 15 g) was obtained. The polymer was found to have an $M_w$ of 15625 g/mol and an $M_n$ of 9592 g/mol. $^1$H NMR showed that the polymer contained 70.6 mol % styrene and 29.4 mol % MMA. Characteristic proton peaks assigned to benzyl alcohol end groups (4.6, 5.1 and 7.3 ppm) were clearly seen and estimated Mn based on proton NMR was in good agreement with Mn obtained from GPC.

Synthesis Example 9

A solution was prepared with 1.88 g of the azo initiator (E)-bis(4-hydroxyphenyl) 4,4'-(diazene-1,2-diyl)bis(4-cyanopentanoate) using method described in Synthesis Example 1, 13.43 g of styrene and 17.16 g of methyl methacrylate dissolved in 76 g of 2-butanone in a 500 mL flask, equipped with a magnetic bar and cold water condenser. After a nitrogen purge for 30 min, the flask was immersed in an 80° C. oil bath. The polymerization reaction was carried out at this temperature for 19 hrs. The reaction solution was then allowed to cool to room temperature and precipitated into methanol. The crude polymer was isolated by filtration, and then purified and isolated by first dissolving it into acetone/2-butanone, re-precipitated with methanol and filtered. Finally the isolated polymer was dried in a 50° C. vacuum oven until constant weight (about 15 g) was obtained. The polymer was found to have an $M_w$ of 16942 g/mol and an $M_n$ of 11813 g/mol. $^1$H NMR showed that the polymer contained 43.4 mol % styrene and 56.6 mol % MMA. Characteristic proton peaks assigned to benzyl alcohol end groups (4.6, 5.1 and 7.3 ppm) were clearly seen and estimated Mn based on proton NMR was in good agreement with Mn obtained from GPC.

Synthesis Example 10

4,4'-Azobis(4-cyanopentanoyl chloride) as an isomer mixture: All procedures were conducted under nitrogen atmosphere. A suspension of 70 g of $PCl_5$ in about 240 ml of dichloromethane was prepared in a round bottom flask with mechanical stirrer. To this suspension, 9.1 g of 4,4'-azobis(4-cyanovaleric acid) were added by portions within 25 minutes. The mixture was stirred for 2 hours at 0-2° C., then 40 hours while it warmed up to 16° C. The excess solid of phosphorus pentachloride was filtered off, washed with $CH_2Cl_2$ (2×10 ml). The resultant solution was concentrated using rotary evaporator at room temperature to give 115 g of colorless liquid. The material was then placed in a freezer at −20° C. for 4 hours. The cold solution was decanted into 200 ml of hexane with good stirring and colorless solid was filtered and well washed with hexane. Yield: 7.3 g (70.8%); m.p. 75-77° C.; $^1$H NMR ($CDCl_3$, δ ppm) 1.68 (s) and 1.74 (s) (6H, 2×$CH_3$, 1:1.21 ratio), 2.4-2.65 (m) and 2.9-3.23 (m) (8H, 2×$CH_2$—$CH_2$, 1:1.14 ratio); $^{13}$C NMR ($CDCl_3$, δ ppm) 23.57 and 23.72 ($CH_3$), 32.87 ($C_q$—$\underline{C}H_2$), 41.67 and 41.77 ($\underline{C}H_2$—C(O)Cl), 71.26 and 71.4 ($C_q$), 116.77 and 116.87 (CN), 172.11 and 172.19 (C(O)Cl).

(2) N,N-bis(diethoxy-phosphorylethyl)amine: A solution was prepared by mixing 5.93 g of diethyl vinylphosphonate with 10 g of concentrated ammonia in a round bottom flask and stirred for 45 hours at room temperature. To the mixture, 40 ml of DI water was added. The product was extracted with dichloromethane (6×7 ml) and the organic phase was dried over $Na_2SO_4$. Stripping off the solvent from the solution afforded 4.1 g (66% yield) of N,N-bis(diethoxyphosphorylethyl)amine as a colorless liquid. $^{13}$C NMR ($CDCl_3$, δ ppm): 16.2 (d, J=6.08 Hz, $CH_3$), 26.3 (d, J=139.32 Hz, $CH_2$—P), 42.8 (d, J=2.76 Hz, $CH_2$—N), 61.4 (d, J=6.08 Hz, $CH_2$—O).

(3) 4,4'-Azobis[4-cyano-N,N-bis(diethoxyphosphorylethyl)pentanoyl amide] as an isomer mixture: A solution was prepared by dissolving 3.68 g of N,N-bis(diethoxy-phosphorylethyl)amine from above (2) and 0.7 g of triethylamine in 23 ml of anhydrous $CHCl_3$ in a round bottom flask. To the solution, 1.69 g of 4,4'-Azobis(4-cyanovaleric acid chloride) from above (1) were added by portions within 15 minutes with stirring for 1 hour at 0-3° C., and then 3 hours while it warmed up to ambient temperature. The reaction mixture was washed with water (5×5 ml) and dried over $Na_2SO_4$. Solvent stripping from the solution in vacuo at room temperature yielded 4.92 g (98%) of yellow-greenish viscous liquid. $^1$H NMR ($CDCl_3$, δ ppm): 1.34 (t, 24H, 8×O—$CH_2$—$C\underline{H}_3$, J=7.04 Hz), 1.65 (s) and 1.74 (s) (6H, 2×$CH_3$, 1:1.2 ratio), 2.02 (m, 8H, 4×$C\underline{H}_2$—P), 2.63-2.34 (m, 8H 2×$C\underline{H}_2$—$C\underline{H}_2$—C(O)), 3.54 (m, 8H, 4×$CH_2$—N), 4.08 (m, 16H, 8×O—$C\underline{H}_2$—$CH_3$);

Example 11

Synthesis of the Phosphonate Terminated Copolymer 1

A solution was made with 1.7923 g of the azo initiator prepared in above example 10 (3), 30 g of styrene and 19.07 g of methylmethacrylate in 80 ml of 2-butanone, in a 250 ml flask equipped with a magnetic stirrer, water condenser and gas bubbler. After nitrogen gas was passed to purge for 30 minutes, the flask was placed in a 76° C. oil bath and stirred for 19 hours. The reaction mixture was cooled to room temperature and the solution was poured slowly into 1.5 L of hexane under stirring. The polymer was isolated by filtration and purified through reprecipitation from 80 ml of 2-butanone solution into 1.5 L of hexane, washed with hexane and dried at 80° C. in a vacuum oven until constant weight of 27.6 g, yield: 56%. Mn 26669 g/mol; Mw 47437 g/mol; PDI (polydispersity) of 1.81.

Example 12

Synthesis of the Phosphonate Terminated Copolymer 2

A solution was made with 2.9271 g of the azo initiator prepared in above example 10 (3), 17.56 g of styrene and 11.13 g of methyl methacrylate in 50 ml of 2-butanone in a flask. It was reacted for 17 hours under same condition described in previous polymer synthesis example 11. After work up, 18.94 g (60%) of polymer was obtained. The polymer was found having Mn 13388 g/mol and Mw 22160 g/mol; and PDI of 1.65.

Example 13

Hydro-de-ethylation of Phosphonate Terminated Copolymer 1 from Example 11 to Form Copolymer 3

A solution was prepared by dissolving 2.62 g of polymer from Example 11 in 8 g of dried dichloromethane. To this solution, 0.22 g of trimethylsilyl bromide was added dropwise within 15 minutes with stirring. The reaction mixture was then put in a 40° C. oil bath for 4 hours. The reaction mixture was cooled to room temperature and poured into methanol (150 ml) to precipitate the polymer. After stirring for 4 hours at room temperature, polymer powder was collected by filtration. The crude polymer was redissolved in 60 ml of dichlorometane and reprecipitated into 400 ml of methanol. The first portion of polymer was collected by filtration. The second portion of the polymer was obtained by stripping off all the solvent from the filtrate in vacuo. After drying in a vacuum oven at 60° C. until constant weight, fraction 1 (1.9 g, 75%) Mn 108,885 g/mol; Mw 673,888 g/mol; fraction 2 (0.65 g, 24.8%) Mn 68984 g/mol; Mw 363094 g/mol.

Example 14

Hydro-de-ethylation of Phosphonate Terminated Copolymer 2 from Example 12 to Form Copolymer 4

A solution 1 was prepared by dissolving 2.82 g of polymer from Example 12 in 23 g of dried dichloromethane. Then solution 2 was prepared by dissolving 0.0745 g of trimethylsilyl bromide in 1.25 g of dried dichloromethane. The solution 2 was then added dropwise to solution 1 within 5 minutes with stirring at room temperature. The reaction mixture was then put in a 40° C. oil bath for 5 hours. The crude was cooled to room temperature and to which 3.6 g of MeOH was added in three portions in a period of 1 hour followed by continued overnight stirring. After stripping off the volatiles, the crude polymer was twice redissolved in 50 ml of 2-Butanone and precipitated in 500 ml hexanes. The final polymer material was filtered and kept in vacuo overnight at room temperature. 2.68 (95%) g of polymer material were obtained, having Mn 11,226 g/mol and Mw 27,257 g/mol; and PDI of 2.43.

Synthesis Example 15

4,4'-Azobis{[4-cyano-N (4-(diethoxyphosphorylmethyl)phenyl]pentanoyl amide} as an isomer mixture A solution was prepared by dissolving 2.15 g of diethyl 4-aminobenzylphosphonate, 1 g of triethylamine in 40 ml of anhydrous $CHCl_3$ in a round bottom flask. To that solution, 1.4 g of 4,4'-Azobis(4-cyanovaleric acid chloride) from example 10 (1) were added by portions within 20 minutes with stirring for 1 hour and 40 minutes at 0-3° C., and then 3 hours while it warmed up to ambient temperature. The reaction mixture was washed with water (5×6 ml) and dried over $Na_2SO_4$. Solvent stripping from the solution in vacuo at room temperature yielded 3.2 g (95%) of solid material. $^1H$ NMR ($CDCl_3$, δ ppm): 1.24t and 1.302t (12H, 4×O—$CH_2$—$CH_3$, J=6.96 Hz), 1.65 s and 1.83 s (6H, 2×$CH_3$, 1:1 ratio), 2.37-2.66 (m, 8H 2×$CH_2$—$CH_2$—C(O)), 3.02 (d) and 3.08 d (4H, 2×$CH_2$—Ar, J=21.56 Hz), 4.02 m (8H, 4×O—$CH_2$—$CH_3$), 6.97 dd (2Har), 7.09 d (2Har), 7.11 dd (2Har) 7.36 d (2Har), 8.98 s (1H, NH) and 9.49 s (1H, NH)

Synthesis Example 16

Synthesis of Phosphonate Terminated Copolymer 4

A solution is made with 1.907 g of the azo initiator prepared in example 15, 4.16 g of styrene and 10.01 g of methyl methacrylate in 40 ml of 2-butanone in a flask equipped with a magnetic stirrer, water condenser and gas bubbler. It is reacted for 17 hours under same condition described in previous polymer synthesis example 11. After work up, 14.8 g (57%) of polymer is obtained. The polymer has a Mn 14798 glmol and Mw 24659 g/mol. PDI: 1.65.

Synthesis Example 17

4.3 g of ammonium salt of 4,4'-azobis(4-cyanovaleric acid) prepared in example 1 was dissolved in a minimum amount of DMSO with stirring. After 2.7 g of epibromohydrin was added, the solution was stirred for 3 days at room temperature. The tetramethylammonium bromide formed was filtered off. The filtrate was slowly poured into stirred DI water. The formed solid was separated by filtering, washed thoroughly with DI water and dried at room temperature in a vacuum oven until constant weight (0.9 g).

0.466 g of azo initiator with epoxy group prepared above, 5.94 g of styrene and 4.41 g of methyl methacrylate were dissolved in 9 g of 2-butanone/22 g THF in a 100 ml flask with a magnetic bar and cold water condenser. After nitrogen purge for 30 minutes, the flask was immersed in 80° C. oil bath. Polymerization reaction was carried out at this temperature for 19 hrs and the reaction solution was allowed to cool to room temperature. The solution was slowly poured in methanol and the obtained polymer was isolated by filtering. The polymer was purified by dissolving in THF and re-precipitated in methanol. Finally the isolated polymer was dried in 50° C. vacuum oven until constant weight (6 g obtained). The polymer was found to have a Mw of 15311 g/mol and a Mn of 10448 g/mol.

Block Copolymer Formulation Example 1

The block copolymer of this example, obtained from DuPont Electronic Polymers (14 TW Alexander Drive, Research Triangle Park, N.C.) (E116389-41) with rated molecular weights 72.6 k-b-40 k (methylmethacrylate) MMA-Sty (styrene) ($M_w$: 112.6K polydispersity (PD): 1.06) was dissolved in propyleneglycol monomethylether acetate (PGMEA) to form a 1.5 wt % solution and filtered through a 0.2 micron PTFE filter.

Block Copolymer Formulation Example 2

The block copolymer of this example, obtained from Polymer Source Inc, (Dorval (Montreal), Quebec, Canada) with rated molecular weights 22 k-b-22 k MMA-Sty ($M_w$: 44K polydispersity (PD): 1.09) was dissolved in PGMEA to form a 1.5 wt % solution and filtered through a 0.2 micron PTFE filter.

Block Copolymer Formulation Example 3

The MMA-Sty block copolymer of around 35 k-b-35 k, was dissolved in PGMEA to form a 1.5 wt % solution and filtered through a 0.2 micron PTFE filter.

Grafting and Neutrality Testing Example 1

A 0.5 wt % solution in PGMEA was prepared with the neutral polymer of Synthesis Example 6 and the thermal acid generator, triethylammonium perfluorobutane sulfonate (5 wt % relative to polymer) and filtered through a 0.2 micron PTFE filter.

The above solution was spin coated at 1500 rpm on a 200 mm Si wafer, baked at 220° C./2 minutes and rinsed with a 70/30 (PGME/PGMEA) solution for 30 sec. Final film thickness was 4.6 nm, indicating that a neutral polymer layer had grafted to the Si substrate. The solution of block copolymer Formulation Example 1 was spin coated atop the resulting film at 3200 rpm to form a 25 nm thick film which was then annealed at 200° C. for 5 minutes. The film was then wet developed with glacial acetic acid for 30 seconds. Scanning electron microscope (SEM) analysis showed vertical cylindrical structures with natural period of 39 nm, an indication of the neutrality of the neutral polymer layer.

Grafting and Neutrality Testing Example 2

A 0.7 wt % solution in PGMEA was prepared with the neutral polymer of Synthesis Example 7 and filtered through a 0.2 micron PTFE filter.

The above solution was spin coated at 1500 rpm on a 200 mm Si wafer, baked at 200° C./5 minutes and rinsed with a 70/30 (PGME/PGMEA) solution for 30 sec. Final film thickness was 5.8 nm, indicating that a brush polymer layer grafted to the Si substrate. The solution of block copolymer Formulation Example 2 was spin coated at 3000 rpm on top of the brush polymer layer to form a 30 nm thick film which was then annealed at 255° C. for 2 min. SEM analysis showed defect-free finger print pattern of the block copolymer, an indication of the neutrality of the neutral polymer layer. Herein the application, a finger print pattern refers to the successful self alignment of the block copolymer to form parallel regions on the substrate, as is known in the art.

Grafting and Neutrality Testing Example 3

A 0.7 wt % solution in PGMEA was prepared with the neutral polymer of Synthesis Example 8 and filtered through a 0.2 micron PTFE filter.

The above solution was spin coated at 1500 rpm on a 200 mm Si wafer, baked at 200° C./5 minutes and rinsed with a 70/30 (PGME/PGMEA) solution for 30 sec. Final film thickness was 6.5 nm, indicating that a brush polymer layer grafted to the Si substrate. The solution of block copolymer Formulation Example 2 was spin coated atop the brush polymer film at 3000 rpm to form a 30 nm thick film which was then annealed at 255° C. for 2 min. SEM analysis showed defect-free finger print of the block copolymer, an indication of the neutrality of the neutral polymer layer.

Grafting and Neutrality Testing Example 4

A 0.7 wt % solution in PGMEA was prepared with the neutral polymer of Synthesis Example 7 and a thermal acid generator (triethylammonium decylbenzene sulfonate, 5 wt % relative to polymer) and filtered through a 0.2 micron PTFE filter.

The above solution was spin coated at 1500 rpm on a 200 mm Si wafer, baked at 200° C./5 minutes and rinsed with a 70/30 (PGME/PGMEA) solution for 30 sec. Final film thickness was 7.5 nm, indicating that a brush polymer layer grafted to the Si substrate. The solution of block copolymer Formulation Example 2 was spin coated atop the brush polymer resulting film at 3000 rpm to form a 30 nm thick film which was then annealed at 255° C. for 2 min. SEM analysis showed defect-free finger print of the block copolymer, an indication of the neutrality of the neutral polymer layer.

Grafting and Neutrality Testing Example 5

A 0.7 wt % solution in PGMEA was prepared with the neutral polymer of Synthesis Example 9 and filtered through a 0.2 micron PTFE filter.

The above solution was spin coated at 1500 rpm on a 200 mm Si wafer, baked at 200° C./5 minutes and rinsed with a 70/30 (PGME/PGMEA) solution for 30 sec. Final film thickness was 6.3 nm, indicating that a brush polymer layer grafted to the Si substrate. The solution of block copolymer Formulation Example 2 was spin coated atop the brush polymer resulting film at 3000 rpm to form a 30 nm thick film which was then annealed at 255° C. for 2 min. SEM analysis showed defect-free finger print of the block copolymer, an indication of the neutrality of the neutral polymer layer.

Grafting and Neutrality Testing Example 6

A 0.7 wt % solution in PGMEA was prepared with the neutral polymer of Synthesis Example 8 and a thermal acid generator (triethylammonium decylbenzene sulfonate, 5 wt % relative to polymer) and filtered through a 0.2 micron PTFE filter.

The above solution was spin coated at 1500 rpm on a 200 mm Si wafer, baked at 200° C./5 min and rinsed with a 70/30 (PGME/PGMEA) solution for 30 sec. Final film thickness was 7.5 nm, indicating that a brush polymer layer grafted to the Si substrate. The solution of block copolymer Formulation Example 2 was spin coated atop the brush polymer resulting film at 3000 rpm to form a 30 nm thick film which was then annealed at 255° C. for 2 min. SEM analysis showed defect-free finger print of the block copolymer, an indication of the neutrality of the neutral polymer layer.

Grafting and Neutrality Testing Example 7

0.7 wt % solution in PGMEA was prepared with the neutral polymer of Synthesis Example 11 and a thermal acid generator (triethylammonium decylbenzene sulfonate, 5 wt % relative to the polymer) and filtered through a 0.2 micron PTFE filter.

The above solution was spin coated at 1500 rpm on a 200 mm Si wafer, baked at 255° C./2 minutes and rinsed with a 70/30 (PGME/PGMEA) solution for 30 seconds. The final film thickness was 4.1 nm, indicating that a brush polymer layer had grafted to the Si substrate. The solution of Block Copolymer Formulation Example 2 was spin coated on top and the resulting film at 1500 rpm gave a 40 nm thick film which was then annealed at 255° C. for 2 minutes. SEM analysis showed defect-free finger print, an indication of the neutrality of the neutral polymer layer.

This Example was repeated using Synthesis Example 12 instead of Synthesis Example 11. SEM analysis showed defect-free finger print, an indication of the neutrality of the neutral polymer layer.

Lithographic Example 1

A 2 wt % solution in PGMEA was prepared with the polymer of Synthesis Example 11 and a thermal acid generator (triethylammonium decylbenzene sulfonate, 5 wt % relative to the polymer) and filtered through a 0.2 micron PTFE filter.

A photoresist pattern was formed. The photoresist pattern had feature size (lines) around 40 nm. The lines were trimmed down to around 15 nm with oxygen plasma etch. The photoresist was removed with a stripper solution in a typical stripping process followed by rinse with de-ionized water. The formulation described above was spin coated on the wafer at 3000 rpm. A bake at 250° C. under nitrogen for 5 minutes was applied to form a film of 35 nm thickness. The coated film was then rinsed with a 70/30 (PGME/PGMEA) solution for 30 seconds followed by a soft bake at 110° C. for 60 seconds to dry the film. Thereafter, the solution of Block Copolymer of Formulation Example 3 was spin coated on top at 3000 rpm to form a 30 nm thick film which was then annealed at 250° C. for 5 minutes. The wafer was analyzed on a CD SEM, Applied Materials Nano 3D. Lamellae aligned to the original photoresist pattern were observed which indicated good neutrality of the novel neutral polymer. Thus, directed self assembly of the block copolymer with the neutral layer was demonstrated.

Lithographic Example 2

A 2 wt % solution in PGMEA was prepared with the polymer of Synthesis Example 8 and filtered through a 0.2 micron PTFE filter.

A photoresist pattern was formed. The photoresist pattern has feature size (lines) around 40 nm. The lines were trimmed down to around 15 nm with oxygen plasma etch. The photoresist was removed with a stripper solution in a typical stripping process followed by rinse with de-ionized water. The formulation described above was spin coated on the wafer at 3000 rpm. A bake at 250° C. under nitrogen for 5 minutes was applied to form a film of 35 nm thickness. The coated film was then rinsed with a 70/30 (PGME/PGMEA) solution for 30 seconds followed by a soft bake at 110° C. for 60 seconds to dry the film. Thereafter, the solution of Block Copolymer Formulation Example 3 was spin coated on top of the resulting substrate at 3000 rpm to form a 30 nm thick film which was then annealed at 250° C. for 5 minutes. The wafer was analyzed on a CD SEM, Applied Materials Nano 3D. Lamellae aligned to the original resist pattern were observed which indicated good neutrality of the invented material. Thus, directed self assembly of the block copolymer with the neutral layer was demonstrated.

Although the present disclosure has been shown and described with reference to particular examples, various changes and modifications which are obvious to persons skilled in the art to which the invention pertains are deemed to lie within the spirit, scope and contemplation of the subject matter set forth in the appended claims.

What is claimed is:

1. A polymeric composition comprising a polymer comprising a) two or more repeat units and b) a terminus having the structure (1)

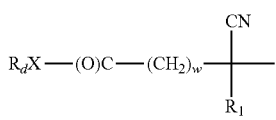
(1)

wherein $R_1$ represents a $C_1$-$C_{20}$ substituted or unsubstituted alkyl group, w is a number from 1-8, X is O or N and $R_d$ is at least one group chosen from i) to viii);

| | | |
|---|---|---|
| i) | 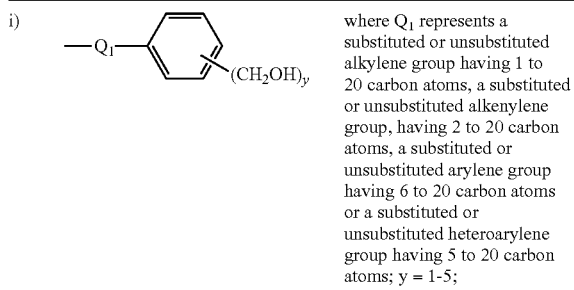 | where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; y = 1-5; |
| ii) | 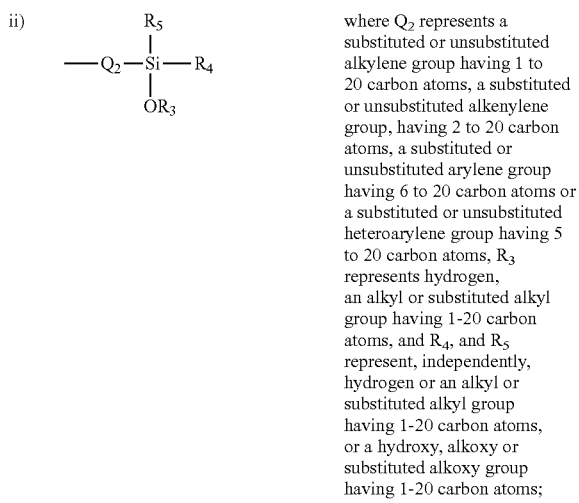 | where $Q_2$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms, $R_3$ represents hydrogen, an alkyl or substituted alkyl group having 1-20 carbon atoms, and $R_4$, and $R_5$ represent, independently, hydrogen or an alkyl or substituted alkyl group having 1-20 carbon atoms, or a hydroxy, alkoxy or substituted alkoxy group having 1-20 carbon atoms; |
| iii) | 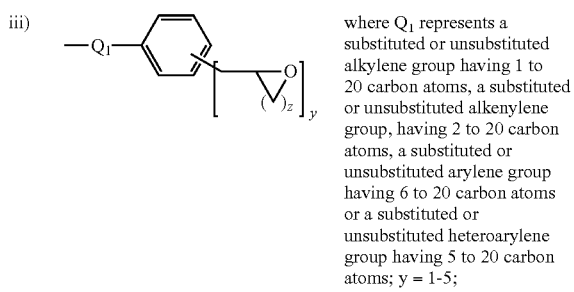 | where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; y = 1-5; |
| iv) | 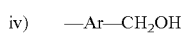 —Ar—CH$_2$OH | where Ar represents a substituted or unsubstituted arylene group having 6 to 20 atoms or a substituted or unsubstituted heteroarylene group having 5 to 20 carbon atoms; |
| v) | 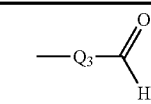 | where $Q_3$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; |
| vi) | 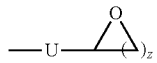 | where U represents a substituted or unsubstituted alkylene group having 1 to 20 carbon atoms; and z is 1-2; |
| vii) | 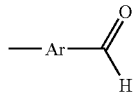 | where Ar represents a substituted or unsubstituted arylene group having 6 to 20 carbon atoms or a substituted or unsubstituted heteroarylene group having 5 to 20 carbon atoms. |
| viii) | 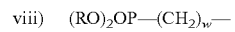 (RO)$_2$OP—(CH$_2$)$_w$— | where R represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms, and w is a number from 1-10. |

2. The polymeric composition of claim 1, where X is oxygen.

3. The polymeric composition of claim 1, where X is nitrogen.

4. The polymeric composition of claim 1, where X is oxygen and $R_d$ is at least one group selected from a group consisting of i) to vii).

5. The polymeric composition of claim 1, where X is oxygen and $R_d$ is at least one group chosen from i) or ii),

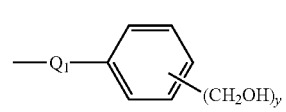
i)

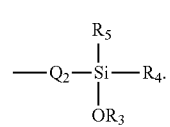
ii)

6. The polymeric composition of claim 1, where X is nitrogen and $R_d$ is at least one group chosen from viii) (RO)$_2$OP—(CH$_2$)$_w$—.

7. The polymeric composition of claim 1, wherein the polymer comprising two or more repeat units is chosen from poly(methylmethacrylate-styrene)poly(butadiene-butylmethacrylate), poly(butadiene-dimethylsiloxane), poly(butadiene-methylmethacrylate), poly(butadiene-vinylpyridine), poly(isoprene-methylmethacrylate), (polyisoprene-vinylpyridine), poly(butylacrylate-methylmethacrylate), poly(butylacrylate-vinylpyridine), (polyhexylacrylate-vinylpyridine), poly(isobutylene-butylmethacrylate), poly(isobutylene-dimethoxysiloxane), poly(isobutylene-methylmethacrylate), poly(isobutylene-vinylpyridine), poly(isoprene-ethyleneoxide), poly(butylmethacrylate-butylacrylate), poly(butylmethacrylate-vinylpyridine), poly(ethylene-methylmethacrylate), poly(methylmethacrylate-butylacrylate), poly(methylmethacrylate-butylmethacrylate), poly(styrene-butadiene), poly(styrene-butylacrylate), polystyrene-butylmethacrylate), poly(styrene-butylstyrene), poly(styrene-dimethoxysiloxane), poly(styrene-isoprene), poly(styrene-methylmethacrylate), poly(styrene-vinylpyridine), poly(ethylene-vinylpyridine), poly(vinylpyridine-methylmethacrylate), poly(ethyleneoxide-isoprene), poly(ethyleneoxide-butadiene), poly(ethyleneoxide-styrene), or poly(ethyleneoxide-methylmethacrylate).

8. The polymeric composition of claim 1, further comprising a thermal acid generator.

9. The polymeric composition of claim 1, further comprising a photoacid generator.

10. The polymeric composition of claim 9, wherein the photoacid generator is an aliphatic or aromatic sulfonium or iodonium salt.

11. A process of forming an image comprising;
   a) forming a neutral layer of the polymeric composition of claim 1 on a substrate;
   b) forming a layer with a solution containing a block copolymer;
   c) annealing the block copolymer thermally so as to allow the block copolymer to undergo directed self assembly;
   d) pattern transferring the self assembled block copolymer using a dry or wet etching process, thereby producing fine patterns.

12. The process of claim 11, where the block copolymer is selected from poly(styrene-b-vinyl pyridine), poly(styrene-b-butadiene), poly(styrene-b-isoprene), poly(styrene-b-methyl methacrylate), poly(styrene-b-alkenyl aromatics), poly(isoprene-b-ethylene oxide), poly(styrene-b-(ethylene-propylene)), poly(ethylene oxide-b-caprolactone), poly(butadiene-b-ethylene oxide), poly(styrene-b-t-butyl(meth)acrylate), poly(methyl methacrylate-b-t-butyl methacrylate), poly(ethylene oxide-b-propylene oxide), poly(styrene-b-tetrahydrofuran), poly(styrene-b-isoprene-b-ethylene oxide), poly(styrene-b-dimethylsiloxane), poly(methyl methacrylate-b-dimethylsiloxane).

13. A polymeric composition, formed by a process, the process comprising:
   a. providing, to a reaction vessel, a salt of 4,4'-azobis(4-cyanovaleric acid), wherein the salt comprises at least one quaternary cation;
   b. providing one or more monomers to the reaction vessel to form a reactive mixture;
   c. heating the reactive mixture at a temperature less than 100° C. for a time of 1-80 hours to form a polymer, then;
   d. providing, to the resulting polymer, a halogenated compound, the halogenated compound chosen from:

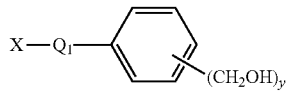

where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms and X represents a halogen; y = 1-5;

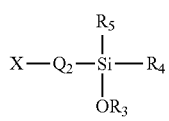

where $Q_2$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms, $R_3$ represents hydrogen an alkyl or substituted alkyl group having 1-20 carbon atoms, and $R_4$, and $R_5$ represent, independently, hydrogen or an alkyl or substituted alkyl group having 1-20 carbon atoms, or a hydroxy, alkoxy or substituted alkoxy group having 1-20 carbon atoms and X represents a halogen;

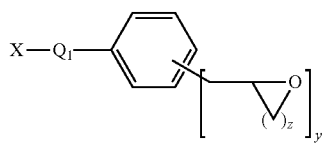

where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms, a substituted or unsubstituted heteroarylene group having 5 to 20 carbon atoms, and y is 1-5 and z is 1-2 and X represents a halogen;

where Ar represents a substituted or unsubstituted arylene group having 6 to 20 carbon atoms or a substituted or unsubstituted heteroarylene group having 5 to 20 carbon atoms and X represents a halogen;

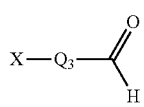

where $Q_3$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms and X represents a halogen;

| | |
|---|---|
| 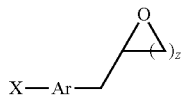 | where Ar represents a substituted or unsubstituted arylene group having 6 to 20 carbon atoms or a substituted or unsubstituted heteroarylene group having 5 to 20 carbon atoms and X represents a halogen; |
| 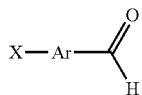 | where Ar represents a substituted or unsubstituted arylene group having 6 to 20 carbon atoms or a substituted or unsubstituted heteroarylene group having 5 to 20 carbon atoms and X represents a halogen. |

14. A functionalized free radical initiator comprising: a compound having the structure

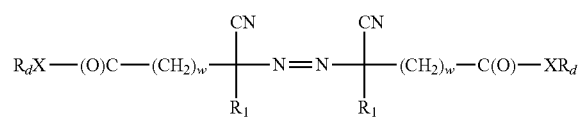

wherein $R_1$ represents a substituted or unsubstituted alkyl group having 1-20 carbon atoms, w is 1-8, X is O or N and $R_d$ is at least one reactive group selected from a group consisting of i) to viii):

| | | |
|---|---|---|
| i) | 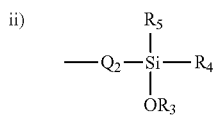 | where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; y = 1-5; |
| ii) | 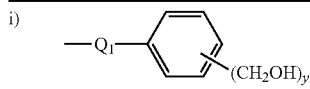 | where $Q_2$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms, $R_3$ represents hydrogen, an alkyl or substituted alkyl group having 1-20 carbon atoms, and $R_4$, and $R_5$ represent, independently, hydrogen or an alkyl or substituted alkyl group having 1-20 carbon atoms, or a hydroxy, alkoxy or substituted alkoxy group having 1-20 carbon atoms; |
| iii) | 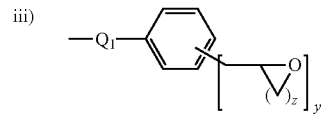 | where $Q_1$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; y = 1-5; |
| iv) | —Ar—CH$_2$OH | where Ar represents a substituted or unsubstituted arylene group having 6 to 20 carbon atoms or a substituted or unsubstituted heteroarylene group having 5 to 20 carbon atoms; |
| v) |  | where $Q_3$ represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms; |
| vi) | 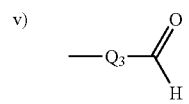 | where U represents a substituted or unsubstituted alkylene group having 1 to 20 carbon atoms; and z is 1-2; |
| vii) | 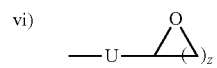 | where Ar represents a substituted or unsubstituted group having 6 to 20 carbon atoms or a substituted or unsubstituted heteroarylene group having 5 to 20 carbon atoms. |
| viii) | (RO)$_2$OP—(CH$_2$)$_w$— | where R represents a substituted or unsubstituted alkylene group having 1 to 20 carbon atoms, a substituted or unsubstituted alkenylene group, having 2 to 20 carbon atoms, a substituted or unsubstituted arylene group having 6 to 20 carbon atoms or a substituted or unsubstituted heteroarylene group having 5 to 20 carbon atoms, and w is a number from 1-10. |

15. A polymeric composition formed by a process comprising:
   e. providing, to a reaction vessel, the functionalized free radical initiator of claim 14;
   f. providing one or more monomers to the reaction vessel to form a reactive mixture; and
   g. heating the reactive mixture at a temperature less than 100° C. for a time of 1-80 hours.

* * * * *